United States Patent [19]

Okumura et al.

[11] Patent Number: 5,536,744
[45] Date of Patent: Jul. 16, 1996

[54] IMIDAZOLINOXYL DERIVATIVES

[75] Inventors: Ken Okumura; Ryusuke Tsunoda; Hiroshi Maeda; Takaaki Akaike; Keizo Sato, all of Kumamoto; Kazumi Sasamoto; Yoshiki Katayama, both of Mashiki-machi, all of Japan

[73] Assignee: Dojindo Laboratories, Japan

[21] Appl. No.: 363,614

[22] Filed: Dec. 23, 1994

[30] Foreign Application Priority Data

Dec. 29, 1993 [JP] Japan ..................... 5-352511

[51] Int. Cl.⁶ ............... A61K 31/415; C07D 233/24; C07D 233/22; C07D 233/20
[52] U.S. Cl. ............. 514/401; 548/348.1; 548/349.1; 548/351.1; 548/352.1
[58] Field of Search ............ 548/348.1, 349.1, 548/351.1, 352.1; 514/401

[56] References Cited

PUBLICATIONS

Tsunoda et al, "Vasodilator effect of carboxy, etc" Eur. J. Pharmacol. (1994), 262 (1–2), 55–63.
Yoshida et al, "Therapeutic effects of, etc" Biochem. Biophys. Res. Commun. (1994), 202(2), 923–30.
Woldman et al, "Spin Trapping of Nitric, etc" Biochem. Biophys. Res Commun (1994), 202(1), 195–203.

*Primary Examiner*—Patricia L. Morris
*Attorney, Agent, or Firm*—Graham & James

[57] ABSTRACT

This invention offers the compounds which exhibit a coronary blood vessel dilating action which is long-acting. (Constitution)

Novel imidazolinoxyl derivatives represented by a general formula (1). A compound A in which R is COOH is given in an example.

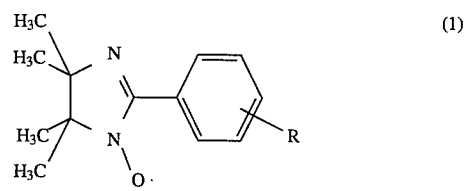

(Merit)

The compounds of the present invention can be directly administered, after diluting to a suitable concentration with a phosphate buffer or the like, to blood vessel which is required to be relaxed and dilated whereby a significant and long-acting relaxing action is resulted though, in a blood flow, they are quickly inactivated and excreted and no side effect is noted.

18 Claims, 5 Drawing Sheets

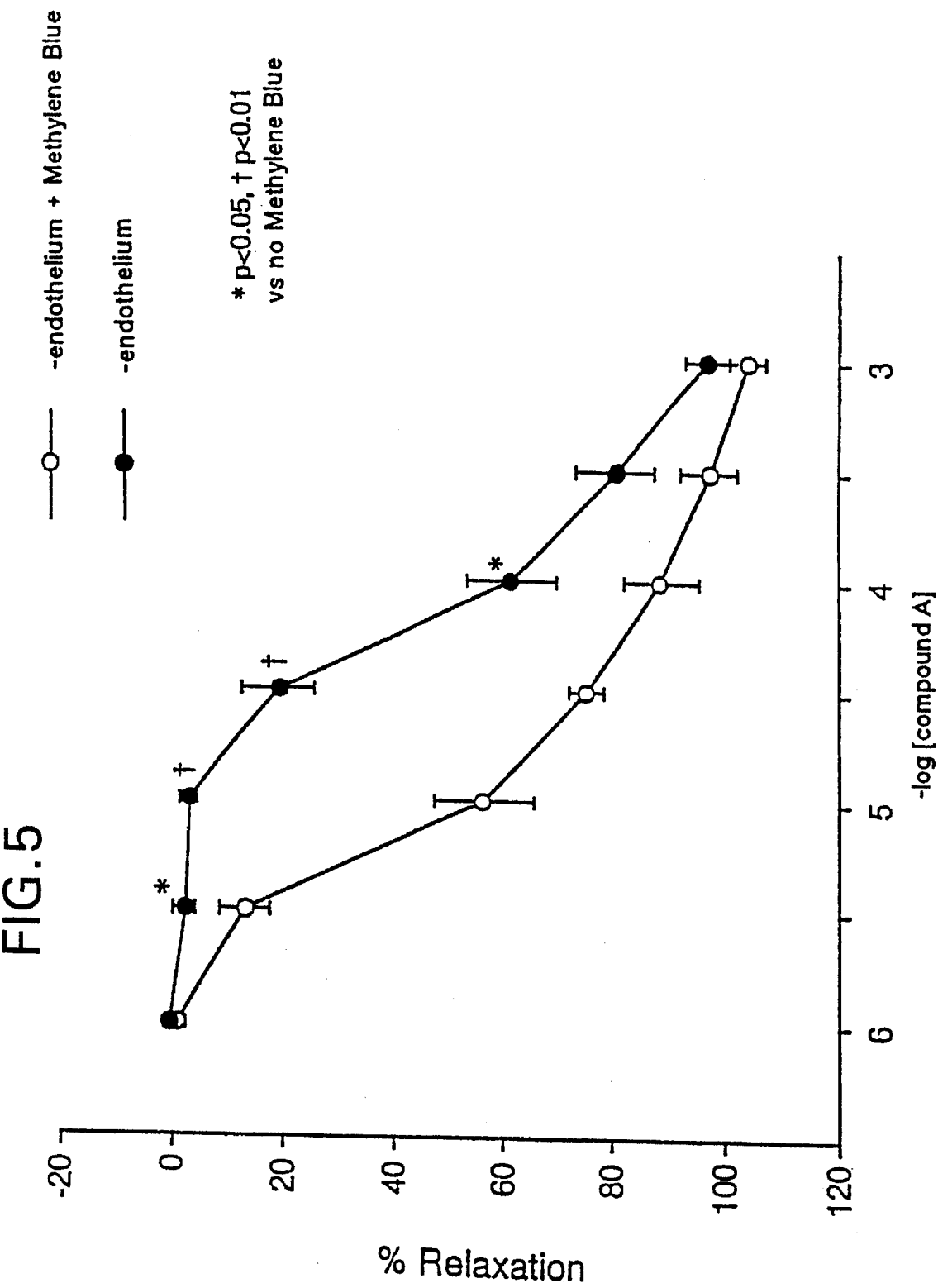

IMIDAZOLINOXYL DERIVATIVES

DETAILED DESCRIPTION OF THE INVENTION

TECHNICAL FIELD

The present invention relates to novel imidazolinoxyl derivatives.

The imidizolinoxyl derivatives which are the compounds of the present invention are novel substances which have not been reported in the prior art literature yet and exhibit a significant vasodilating action. A method of dilating the blood vessel using said compounds is useful in a medical diagnosis.

PRIOR ART

Organic nitro compounds such as nitroglycerol and blockers for calcium channel such as nifedipine have been known as coronary vasodilators though all of them are with a relative toxicity and exhibit side actions such as systemic arterial hypotension. In addition, the action of the widely-used dilators such as nitroglycerol is transient and is not long-acting.

(Problems to be Solved by the Invention)

An object of the present invention is to offer certain compounds which exhibit coronary vasodilating action in which said action is limited to the blood vessel to which the compound is administered and, moreover, said action is long-acting.

(Means to Solve the Problems)

Thus, the novel compounds of the present invention are the imidazolinoxyl derivatives which are represented by a general formula (1)

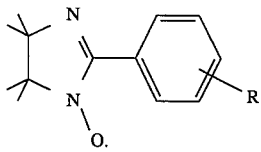

(in which R is COOH, O(CH$_2$)$_n$COOH (n=1–3), SO$_3$H or N(CH$_3$)$_3^+$,

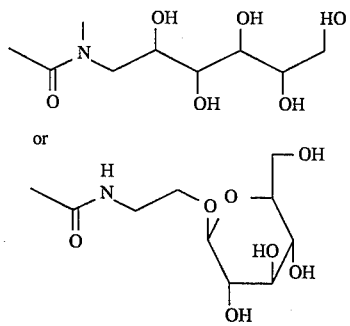

locating at 3- or 4-position to the imidazolinoxyl group) or salts thereof.

The present invention also includes the use of the above-mentioned compounds as a coronary vasodilator by dissolving, for example, in a phosphate buffer in a suitable concentration followed by a direct administration to blood vessel which is required to be relaxed or dilated such as, for example, coronary arteries.

The compounds represented by the general formula (1) may be synthesized as follows. Thus, a compound represented by the following general formula (2) is made to react with a compound represented by a general formula (3) (wherein R has the same meaning as defined already), the resulting compound of a general formula (4) is heated in N,N-dimethylformamide and the resulting compound of a general formula (5) (wherein R has the same meaning as defined already) is oxidized with manganese dioxide.

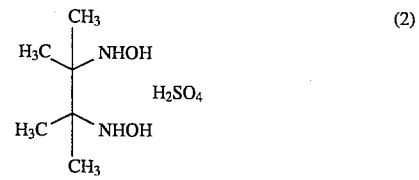

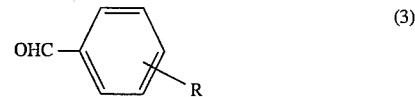

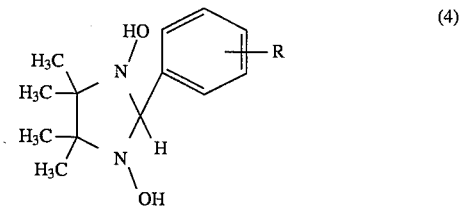

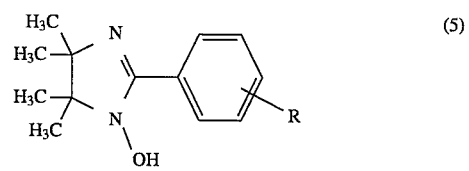

All of the compounds A to F given as hereunder which are specific examples of the compounds of the present invention represented by a general formula (1) which are prepared as such are solids in orange color with a high solubility in water.

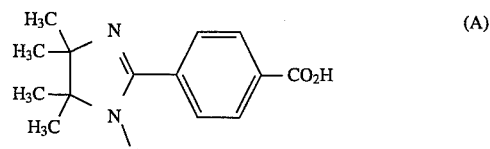

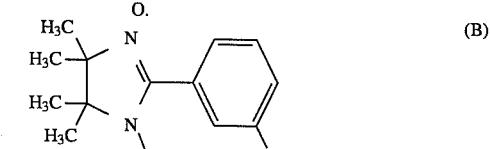

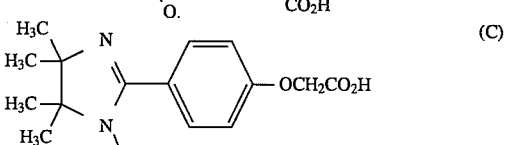

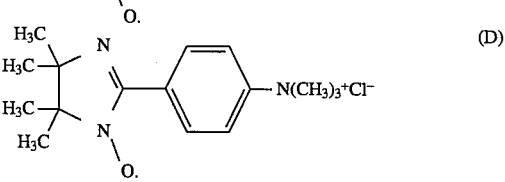

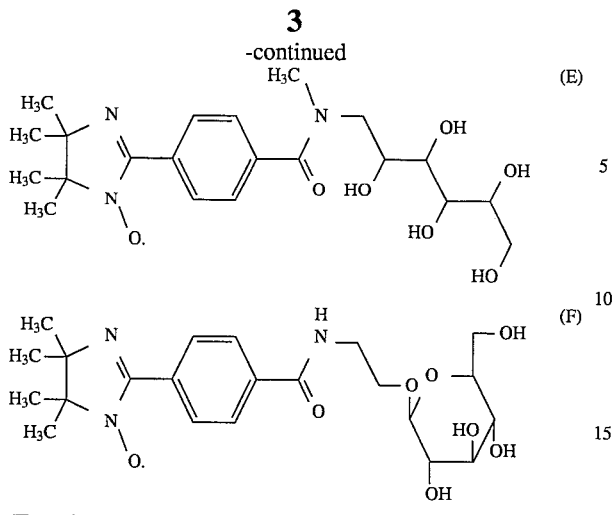

(Function)

All of those compounds have an N-oxyl radical in a molecule and they significantly relax the coronary vessel to which the compound is administered.

Moreover, although the resulting effect is prompt and long-acting, the compound is excreted outside the body together with a quick inactivation in a blood flow. In other words, although its action in coronary blood vessel to which the compound is administered is significant, there is no affection on other parts of the body. Accordingly, side actions such as a blood pressure reduction and those on cardiac beats and on contractive force of heart are not noted at all.

Because of the object of the present invention and the nature of the compound of the invention, it is preferred that the compound of this invention is directly administered to the blood vessel or to some other area so that the compound at last comes to the blood vessels.

In order to achieve a quick and sure action, it is preferred to administer the compound to a blood vessel directly and, particularly preferably, to an artery.

With respect to the administering means, injection is the most preferred although other means such as instillation or drip infusion may be applied if necessary either solely or together with an injection into an artery.

With respect to the dosage amount, it is preferred to obtain a concentration of the compound in the artery of about 0.001–100 mM, preferably 0.01–10 mM, most preferably 0.1–1.0 mM. Although the actual amount to be administered to the patient may vary depending upon the symptoms and circumstances. The dosage may be 0.01–500 mg of the compound per kg of body weight of the patient, preferably 0.1–50 mg/kg, most preferably 1–10 mg/kg.

Principally, the compound is to be administered when a dilation of the blood vessel is required. Accordingly, it is most common that the administration is conducted only one when such a requirement arises. However, depending upon the symptoms and circumstances, the compound may be administered twice or more with certain intervals.

The above mentioned description is given for the purpose of exemplification only and, therefore, this invention is not limited thereto.

BRIEF EXPLANATION OF THE DRAWINGS

FIG. 5 shows an effect of Methylene Blue on a coronary artery relaxation of the compound A.

EXAMPLES

Figure 1:
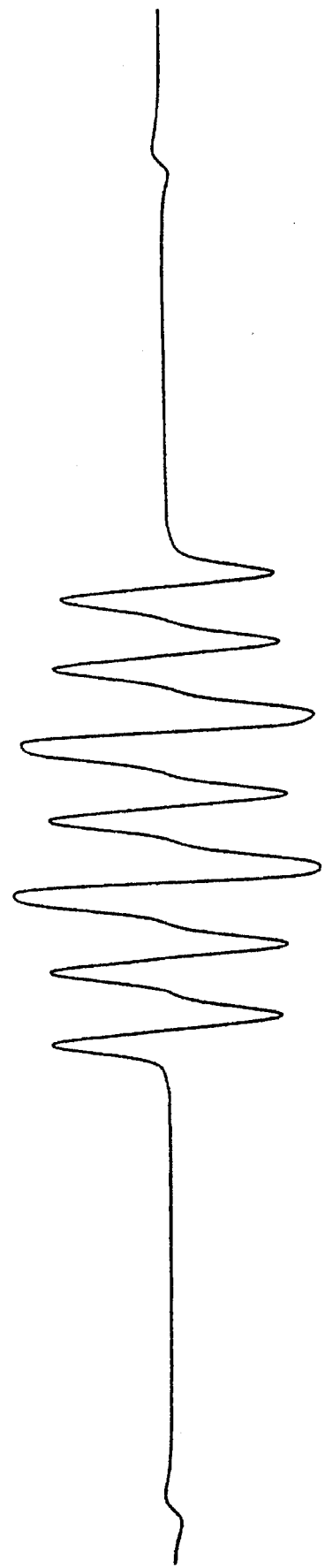
FIG. 1 is an electron spin resonance (ESR) spectrum of the compound A of the present invention.

Synthetic examples (Examples 1 to 5) of the compounds of the present invention and the pharmacological tests (Examples 6 to 8) on coronary vessel using those compounds are specifically given as hereunder by means of working examples and the present invention is not limited thereby.

Various measurements in the following examples were carried out using the following devices.

Ultraviolet-visible absorption spectrum: UV-260 manufactured by Shimadzu Corporation.

Electron spin resonance (ESR) spectrum: JES-FR80 manufactured by JEOL Limited. Frequency number of the microwave: 9.416 GHz; microwave power: 5mW; magnetic field: 335.2 mT±5 mT.

Example 1

(Synthesis of the compound A)

2,3-Bis(hydroxyamino)-2,3-dimethylbutane sulfate (3.34 g) was suspended in 14 ml of pure water and the suspension was cooled at 0° C. and 6.8 ml of 20% aqueous solution of potassium bicarbonate and 2.04 g of 4-formylbenzoic acid were gradually added thereto. After that, 14 ml of a 20% aqueous solution of potassium bicarbonate was added and the mixture was stirred overnight at room temperature. White precipitate of the compound corresponding to the general formula (4) was collected by filtration, washed with cold water and dried.

Then the product (1.47 g) was heated with stirring under refluxing in a mixed solvent comprising 20 ml of N,N-dimethylformamide and 100 ml of methanol for 46 hours. After that, the resulting precipitate was collected by filtration and washed with methanol. In the meanwhile, the filtrate was concentrated, 6 ml of N,N-dimethylformamide and 30 ml of methanol were added to the concentrate and the resulting precipitate was collected by filtration and washed with methanol.

The resulting compound (950 mg) corresponding the general formula (5) prepared as such was oxidized with an activated manganese dioxide in N,N-dimethylformamide to give 760 mg of the compound A.

Properties of the resulting compound A were as follows.

External appearance: Powder in an orange color.

Ultraviolet-visible absorption spectrum: $\lambda_{max}$=242 nm ($\epsilon$: 17,700), 432 nm ($\epsilon$: 590).

ESR spectrum: given in FIG. 1.

Example 2

(Synthesis of the Compound B)

2,3-Bis(hydroxyamino)-2,3-dimethylbutane sulfate (820 mg) was suspended in 3.3 ml of pure water, the solution was cooled at 0° C. and 1.7 ml of a 20% aqueous solution of potassium bicarbonate and 500 mg of 3-formylbenzoic acid were gradually added thereat. Then 3.3 ml of a 20% aqueous solution of potassium bicarbonate was added followed by stirring at room temperture for overnight. A white precipitate of a compound correponding to the general formula (4) was collected by filtration, washed with cool water and dried.

Then the product (350 mg) was heated with stirring to reflux in a mixed solvent comprising 4.5 ml of N,N-dimethylformamide and 24 ml of methanol. The resulting precipitate was collected by filtration and washed with methanol. The filtrate was further concentrated and the precipitate was collected by filtration by adding 1.5 ml of N,N-dimethylformamide and 7 ml of methanol followed by washing with methanol.

The compound (210 mg) corresponding to the general formula (5) prepared as such was oxidized with an activated manganese dioxide in N,N-dimethylformamide to give 176 mg of a compound B.

Physical properties of the resulting compound B were as follows.

External appearance: Powder in an orange color

Ultraviolet visible absorption spectraum: $\lambda_{max}$=238 nm ($\epsilon$: 17,500), 432 nm ($\epsilon$: 580).

ESR spectrum: (like that of FIG. 1)

Example 3

(Synthesis of the Compound C)

2,3-Bis(hydroxyamino)-2,3-dimethylbutane sulfate (2.46 g) was suspended in 10 ml of pure water, the suspension was cooled at 0° C. and 5 ml of a 20% aqueous solution of potassium bicarbonate and 1.8 g of 4-formylphenoxyacetic acid were gradually added thereto. After that 10 ml of a 20% aqueous solution of pottasium bicarbonate was added followed by stirring at room temperature for overnight. A white precipitate of a compound corresponding to the general formula (4) was collected by filtration, washed with cool water and dried.

Then the product (1.03 g) was heated with stirring to reflux in a mixed solvent comprising 13.5 ml of N,N-dimethylformamide and 71 ml of methanol. After that, the precipitate was collected by filtration and washed with methanol. The filtrate was further concentrated and the precipitate was collected by filtration after adding 4.4 ml of N,N-dimethylformamide and 21 ml of methanol followed by washing with methanol.

The compound (650 mg) corresponding to the general formula (5) prepared as such was oxidized with an activated manganese dioxide in N,N-dimethylformamide to give 510 mg of the compound B.

Physical properties of the resulting compound B were as follows

External appearance: Powder in an orange color

Ultrviolet visible absorption spectrum: $\lambda_{max}$=243 nm ($\epsilon$: 17,700), 432 nm ($\epsilon$: 600)

ESR spectrum: (like that of FIG. 1)

Example 4

(Synthesis of the compound D)

p-Dimethylaminobenzaldehyde (5 g) was stirred under refluxing in 50 ml of methyl iodide for overnight. The resulting pale yellow precipitate was collected by filtration, washed with chloroform and dried to give 3.4 g of a compound corresponding to the general formula (3).

Then 1.27 g of 2,3-bis(hydroxyamino)-2,3-dimethylbutane sulfate was suspended in 5.3 ml of pure water, the suspension was cooled to 0° C. and 2.75 ml of a 20% aqueous solution of potassium bicarboane and 1.5 g of trimethylammonium benzaldehyde iodide were gradually added thereto. After that, 5 ml of aqueous solution of potassium bicarbonate was added and the mixture was stirred at room temperature for one night. White precipitate of a compound corresponding to the general formula (4) was collected by filtration, washed with cold water and dried to give 1.38 g of white powder.

Then the resulting compound was treated with an anionic ion-exchange resin of a chloride ion type (Dowex 1-X8) to make a chloride ion type compound. This (850 mg) was stirred by heating under refluxing for 46 hours in a mixed solvent comprising 8 ml of N,N-dimethylformamide and 40 ml of methanol. The precipitate was collected by filtration and washed with methanol. The filtrate was concentrated, 2 ml of N,N-dimethylformamide and 10 ml of methanol were added thereto and the resulting precipitate was collected by filtration followed by washing with methanol.

The compound (500 mg) corresponding to the general formula (5) prepared as such was oxidized with an activated manganese dioxide in N,N-dimethylformamide to give 390 mg of the compound D.

Properties of the resulting compound D were as follows.

External appearance: Solid in orange color.

Ultraviolet-visible absorption spectrum: $\lambda_{max}$=245 nm ($\epsilon$: 17,000).

ESR spectrum: same as that given in FIG. 1.

Example 5

(Synthesis of the compound E)

4-Formylbenzoic acid (500 mg) and 637 mg of triethylamine were added to 10 ml of N,N-dimethylformamide and 343 μl of ethyl chlorocarbonate cooled at 0° C. was dropped thereinto. After stirring the mixture for 30 minutes, a solution of 700 mg of N-methylglucamine in 5 ml of N,N-dimethylformamide was dropped thereinto and the temperature of the mixture was ajusted to a room temperature followed by stirring the mixture overnight. After that, it was concentrated and the concentrate was purified by a column chromatography on silica gel using 10% methanolic chloroform as an eluting solvent followed by recrystallizing from chloroform to give 480 mg of N-methylglucamidobenzaldehyde corresponding to the general formula (3) as a pale yellow solid.

Then 150 mg of 2,3-bis(hydroxyamino)-2,3-dimethylbutane sulfate was suspended in 1.5 ml of pure water, the suspension was cooled at 0° C. and 0.3 ml of 20% aqueous solution of potassim bicarbonate and 200 mg of N-methylglucamidobenz-aldehyde were gradually added thereto. After that, 0.3 ml of an aqueous solution of potassium bicarbonate was added thereto and the mixture was stirred overnight at room temperature. This was then concentrated, the concentrate was dissolved in methanol to remove inorganic salts therefrom and the solution was purified by means of a chromatography using 20% methanolic chloroform to give 110 mg of a white solid.

This was stirred under refluxing for 46 hours in a mixed solvent comprising 1 ml of N,N-dimethylformamide and 5 ml of methanol. After that, the resulting precipitate was collected by filtration while the filtrate was concentrated followed by adding 0.5 ml of N,N-dimethylformamide and 4 ml of methanol thereto to collect the precipitate by filtration.

The compound (60 mg) corresponding to the general formula (5) prepared as such was oxidized with an activated manganese dioxide in N,N-dimethylformamide to give 43 mg of the compound E.

Properties of the resulting compound E were as follows.

External appearance: Powder in an orange color.
Ultraviolet-visible absorption spectrum: $\lambda_{max}$=248 nm ($\epsilon$: 16,800).
Infrared absorption spectrum (cm$^{-1}$): 3450, 1600, 1550, 1420, 1392, 1364.
ESR spectrum: same as that given in FIG. 1.

Example 6

(Test on the relaxation of coronary arteries using the compound A)

Twenty mongrel adult dogs were anesthetized with 30 mg/kg pentobarbital, their breasts were opened under an artificial respiration and heparin (3,000 IU/kg; each 1,000 IU/mg administered intravenously every 30 minutes thereafe) and aspirin (17 mg/kg) were administered. Then a cannula was inserted near the circumflex branch of the left coronary artery and a perfusion was conducted by means of a bypath from the whole left carotid artery. Coronary blood flow was measured, by an electromagnetic blood flowmeter (MFV-3200 manufactured by Nippon Koden) via a probe for measuring the blood flow (manufactured by Nippon Koden) located at the center of the bypath while the artery pressure and the left cardiac pressure were measured at an underarm artery and by means of a catheter inserted from the apex, respectively.

Figure 2:
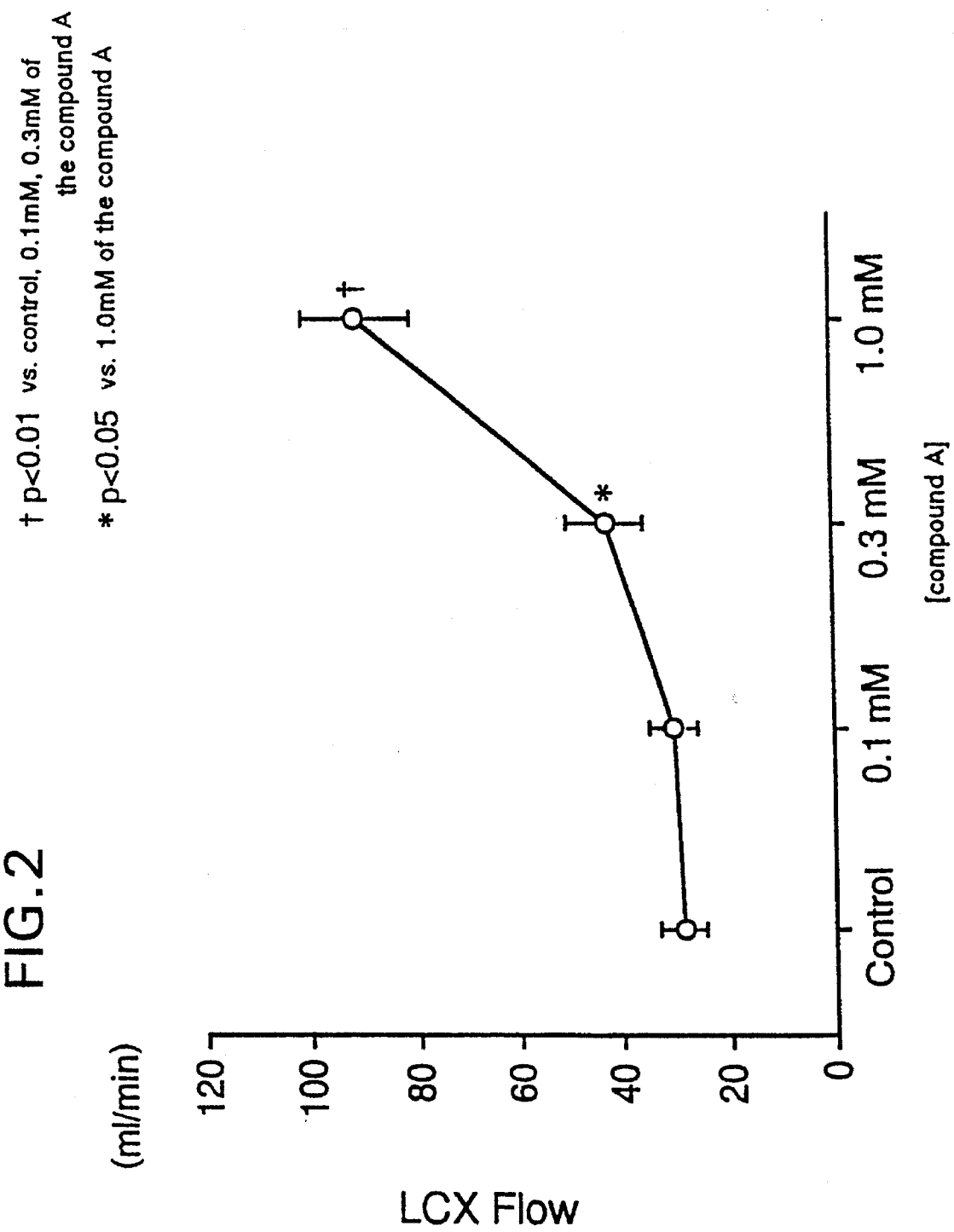
FIG. 2 shows an effect of the compound A on the coronary flow rate.

After the blood flow status was stabilized, a compound A which was dissolved in a phosphate buffer (10 mM; pH 7.4) to make the concentration 30 mM was administered for four minutes in a stepwise manner whereby the concentration in the coronary artery becomes 0.1, 0.3 and 1.0 mM and the changes in the coronary blood flow and the blood flow status were observed. The result was that, as shown in FIG. 2, there was a significant increase in the coronary blood flow and, upon the administration of 1 mM for four minutes, the increase was about three times as much (an increasing rate: ca. 200%). In addition, this effect lasted at least for 30 minutes after completion of the administration.

Further, as shown in Table 1, there were no change in the pulse numbers, the blood pressure and the pressure at the final stage of the left cardiac dilation and no side effect was noted in spite of a significant relaxation. Rather, the left cardic dp/dt had an increasing tendency and the contracting power of the heart was rather improved.

In order to check such a low side effect, the behavior of the compound A in blood flow was investigated.

Thus, within a certain period after the administration, samples of blood and urine were collected and "a concentration of the compound A which was unchanged and retained" and "a total concentration after oxidization with potassium ferricyanide" were determined by means of an electronic spin resonance (RF80; Nippon Denshi). As a result thereof, it was found that the compound A was quickly reduced by ascorbic acid, etc. in blood to loose an N-oxyl radical in a reversible manner and that the compound A and its reduced product were rapidly excreted from the kidney whereby their clearance was very prompt. The total amount of the compound A remaining in the blood at one minute after the administration was only about 0.3%. Accordingly, the compound A acted only at the blood of the part to which the compound was administered and did not affect on other parts of the body whereby no side effect was noted.

TABLE 1

Effect of the Compound A on the Coronary Blood Flow and on the Behavior of the Blood Flow

| | Concentration of Compound A in Artery | | | |
| --- | --- | --- | --- | --- |
| | 0 (Control) | 0.1 mM | 0.3 mM | 1.0 mM |
| Blood Flow at Rotation Branch (ml/min) | 28.7 ± 3.3 | 29.8 ± 3.6 | 41.5 ± 5.7* | 89.7 ± 10.6** |
| Pulse Numbers (/min) | 155 ± 9 | 155 ± 8 | 154 ± 8 | 157 ± 8 |
| Av.Blood Pressure(mmHg) | 129 ± 7 | 130 ± 8 | 133 ± 8 | 132 ± 7 |
| Pres.at Final Stage of Left Cardiac Dilation (mmHg) | 10 ± 2 | 11 ± 2 | 10 ± 2 | 10 ± 2 |
| Left Cardiac dp/dt (mmHg/sec) | 1132 ± 79 | 1132 ± 60 | 1210 ± 63 | 1241 ± 50 |

The above numbers are the average values by means of an analysis of varience and the standard error ranges.
*$p < 0.05$ to the control
**$p < 0.01$ to the control, 0.1 mM and 0.3 mM Comparative Example 1

Figure 3:
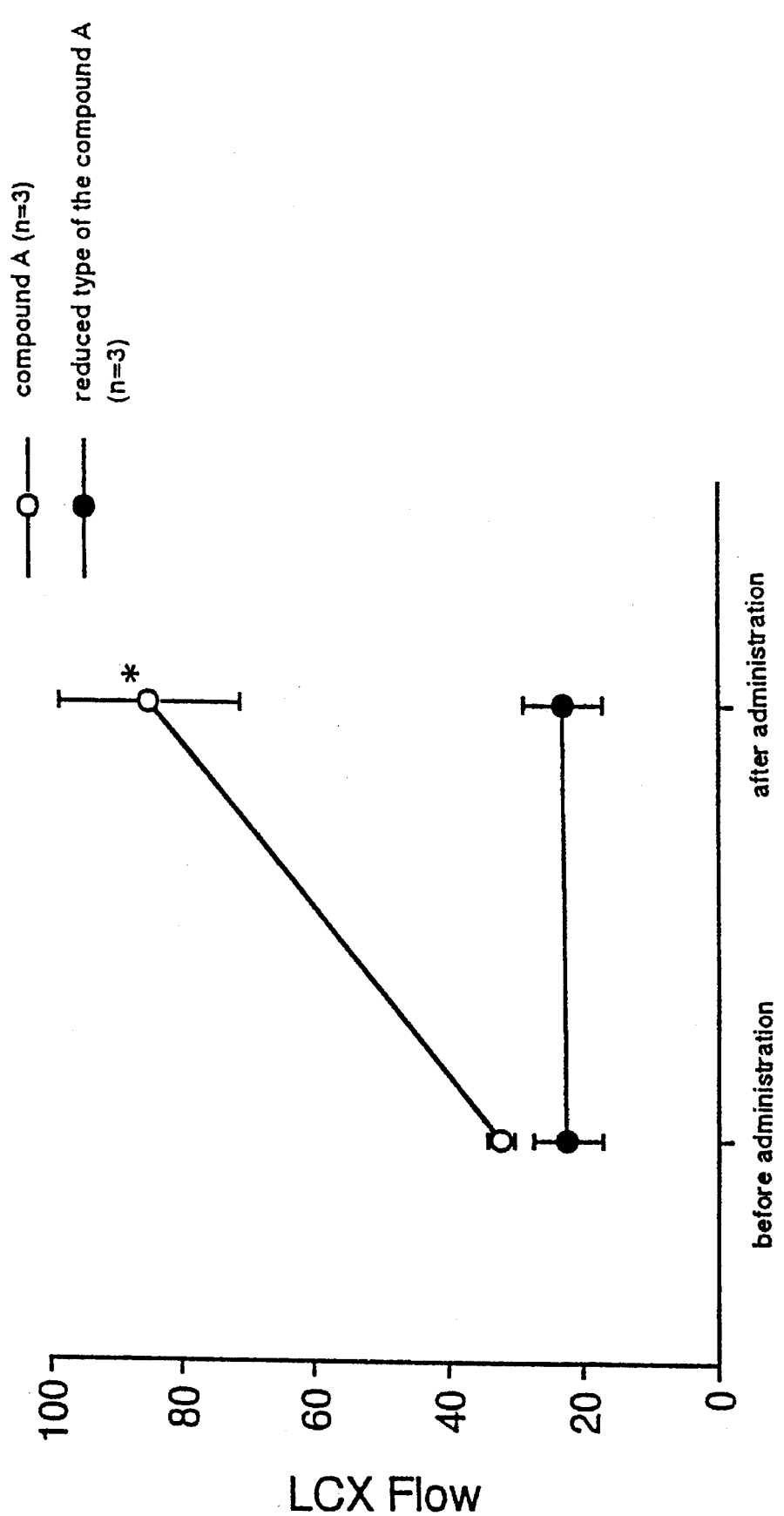
FIG. 3 shows an effect of compound A (1.0 mM) and a reduced type thereof (1.0 mM) in which n is the numbers of the mongrel dogs used for the experiment.

The operation of Example 4 was conducted by administering the compound A wherefrom the N-oxyl radical was inactivated only after reducing with ascorbic acid. The pharmacological action found in Example 4 has completely disappeared and, as shown in FIG. 3, there was no changes in the blood flow before (22.4 ml/minute) and after (22.8 ml/minute) the administration. It is therefore apparent that the pharmacological action was due to the radical in the molecule and that the compounds of the present invention are the pharmaceuticals of a new type.

Example 7

(Effect of Various Pharmaceuticals)

The compound A was administered for four minutes, by the same manner as in Example 6, to a control group, to a group (LNAME-treated group) which was pretreated with a methyl ester of NG-nitro-L-arginine which was an inhibitor for the production of nitrogen monoxide caused by endothelium (by administering to the coronary artery at the dose of 200 μM for six minutes), to a group (8PT-treated group) which was pretreated with 8-phenyltheophylline which was an adenosnine antagonist (by administering to the coronary artery at the dose of 30 ng/kg/minute) an a group (autonomic nerve blocking group) which was pretreated with a pharmacological autonomic blocking agent (by an intravenous administration of 0.1 mg/kg of atropine, 1 mg/kg of propranolol and 2 mg/kg of phentolamine) to make the concentration of the compound A in the coronary artery 1.0 mM whereby the results were compared.

The results were that, as shown in Table 2, none of the pharmaceuticals affected on the action of the compound A and, therefore, it is apparent that any of those routes does not participate in the action mechanism of the compounds of the present invention.

TABLE 2

Effect of Various Pharmaceuticals on a Coronary Blood Flow Increase by Administration of the Compound A (1.0 mM in Artery)

| | Blood Flow in Rotary Branch (ml/min) | | |
|---|---|---|---|
| | Administration of Compd A | | % Increase |
| | Before | After | |
| Control Group | 32.0 ± 2.1 | 84.9 ± 13.7 | 164 ± 31 |
| LNAME-Treated Group | 26.1 ± 2.7 | 67.0 ± 11.5 | 155 ± 28 |
| 8 PT-Treated Group | 23.1 ± 2.7 | 51.6 ± 5.8 | 120 ± 10 |
| Autonomic Nerve Blocked Gr. | 19.5 ± 3.3 | 49.3 ± 18.5 | 137 ± 56 |

Example 8

(Investigation of Pharmacological Action by Means of an in vitro Test)

After an anesthetization of the mongrel adult dogs, the extracted ring samples (outer diameter: about 2 mm) of the circumflex branch were prepared, hung in a chamber filled with 3 ml of a Krebs buffer which was oxidated (with 95% oxygen and 5% carbon oxide), balanced with an initial tension of 2 g and subjected to a precontraction by prostaglandin F2α (concentration in the chamber: 2 μM).

To this was added the compound A on an accumulated manner whereby its concentration in the chamber became from 1 μM to 1 mM and the resulting changes in the isometric tension were measured using a tranducer (manufactured by Minebea) and recorded in a pen recorder (SR6211 manufactured by Graphtec). Incidentally, the changes in the tension were evaluated on a basis that the precontraction by prostaglandin F2α was 100%. In some of the samples, the endothelium was exfoliated (confirmed by a disappearance of the relaxation to 1 μM of acetylcholine) and, furthermore, they were subjected to a pretreatment with Methylene Blue, an inhibitor for a soluble guanylate cyclase, (concentration in the chamber: 10 μM; administered 30 minutes before) whereby the effect was investigated.

Figure 4:
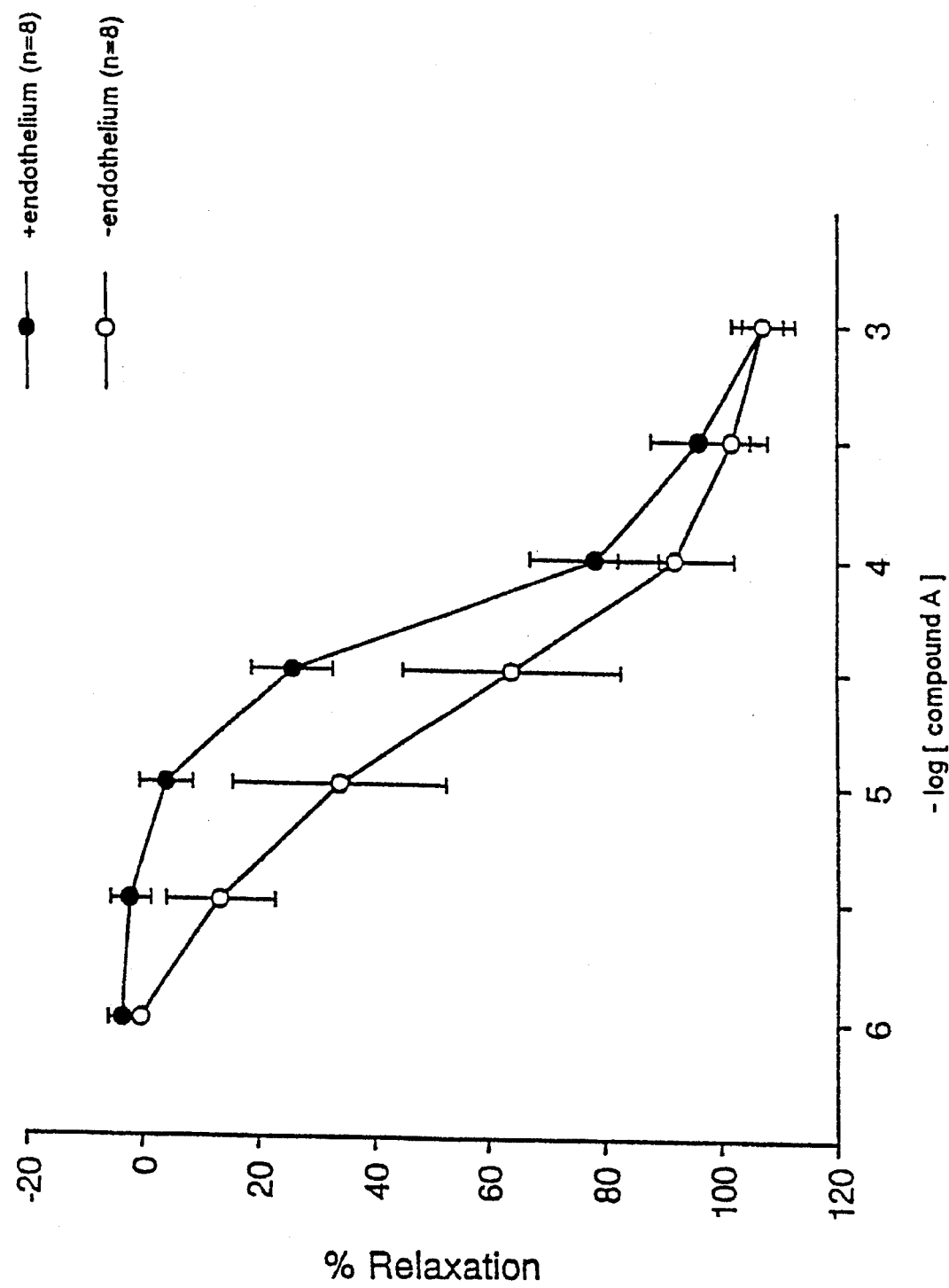
FIG. 4 shows an influence of the endothelium on a coronary artery relaxation of the compound A in which n is the numbers of the mongrel dogs used for the experiment.

The result was that, as shown in FIG. 4, there was a tendency that the action of the compound A was stronger than that in the absence of the endothelium and it is likely that the pharmacological action is due to a direct action to the smooth muscle of the blood vessel.

Then an investigation was conducted for finding a substance which antagonizes and inhibits the pharmacological action of the compound A in a system where the endothelium was absent whereby Methylene Blue which was an inhibitor for guanylate cyclase was found to inhibit that. Thus, in FIG. 5 in which the effect of Methylene Blue to the coronary artery relaxing action of the compound A is shown, the $ED_{50}$ value of the compound A expressed in terms of a minus logarithm of the administered concentration was 5.0+0.1 when no Methylene Blue was added while it changed to 4.1+0.1 (p<0.01) upon administration of Methylene Blue.

Therefore, it is supposed that the compounds of the present invention activated the guanylate cyclase on a continued basis whereby the blood vessel was continuously relaxed.

As mentioned hereinabove, the compounds of the present invention do not exhibit a side effect by a direct administration to blood vessel and, in addition, do not exhibit a toxicity even by oral administration to rats at the concentration of 100 mM.

(Merit of the Invention)

As shown in the above examples, the compounds of the present invention directly act on a smooth muscle of the blood vessel to which the compounds are administered to continuously activate the guanylate cyclase whereby the relaxation of the blood vessel to which the compounds are administered was made sustained.

The compounds of the present invention do not remain in the blood flow but are excreted quickly whereby the side action by their administration are not substantially noted and the method of dilating the blood vessel using such a method is extremly useful in a medical diagnosis.

What is claimed is:

1. An imidazolinoxyl derivative represented by the following formula (1):

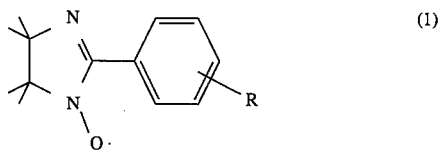

(in which R is COOH, O(CH$_2$)$_n$COOH (n=1–3), SO$_3$H or N(CH$_3$)$_3$$^+$, or

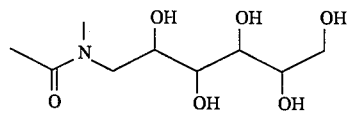

locating at 3- or 4-position to the imidazolinoxyl group) or pharmaceutically acceptable salts thereof.

2. The imidazolinoxyl derivative of claim 1, represented by the following formula (A):

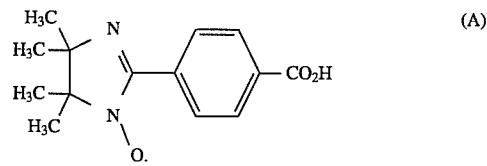

3. The imidazolinoxyl derivative of claim 1, represented by the following formula (B):

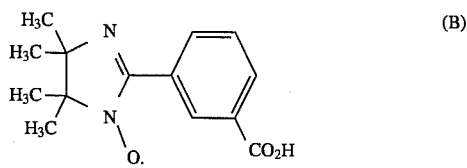

4. The imidazolinoxyl derivative of claim 1, represented by the following formula (C):

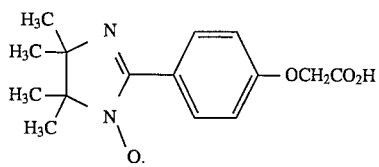

5. The imidazolinoxyl derivative of claim 1, represented by the following formula (D):

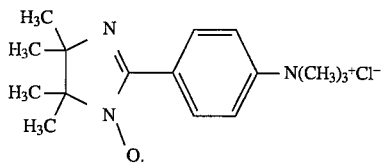

6. The imidazolinoxyl derivative of claim 1, represented by the following formula (E):

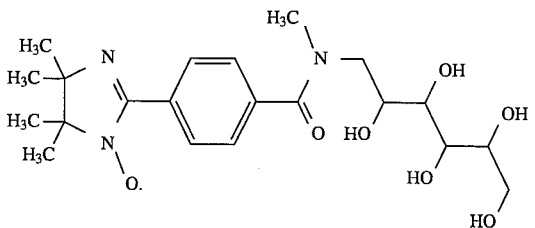

7. A method for obtaining a coronary artery vasodilating effect in a human or animal in need thereof, which comprises administering to said human or animal an effective amount of the compound according to claim 1.

8. A method for obtaining a coronary artery vasodilating effect in a human or animal in need thereof, which comprises administering to said human or animal, an effective amount of the compound according to claim 2.

9. A method for obtaining a coronary artery vasodilating effect in a human or animal in need thereof, which comprises administering to said human or animal an effective amount of the compound according to claim 3.

10. A method for obtaining a coronary artery vasodilating effect in a human or animal in need thereof, which comprises administering to said human or animal an effective amount of the compound according to claim 4.

11. A method for obtaining a coronary artery vasodilating effect in a human or animal in need thereof, which comprises administering to said human or animal an effective amount of the compound according to claim 5.

12. A method for obtaining a coronary artery vasodilating effect in a human or animal in need thereof, which comprises administering to said human or animal an effective amount of the compound according to claim 6.

13. A pharmaceutical composition for obtaining a coronary artery vasodilating effect in a human or animal in need thereof, which comprises an effective amount of the compound according to claim 1 and a pharmaceutically acceptable diluent or carrier therefor.

14. A pharmaceutical composition for obtaining a coronary artery vasodilating effect in a human or animal in need thereof, which comprises an effective amount of the compound according to claim 2 and a pharmaceutically acceptable diluent or carrier therefor.

15. A pharmaceutical composition for obtaining a coronary artery vasodilating effect in a human or animal in need thereof, which comprises an effective amount of the compound according to claim 3 and a pharmaceutically acceptable diluent or carrier therefor.

16. A pharmaceutical composition for obtaining a coronary artery vasodilating effect in a human or animal in need thereof, which comprises an effective amount of the compound according to claim 4 and a pharmaceutically acceptable diluent or carrier therefor.

17. A pharmaceutical composition for obtaining a coronary artery vasodilating effect in a human or animal in need thereof, which comprises an effective amount of the compound according to claim 5 and a pharmaceutically acceptable diluent or carrier therefor.

18. A pharmaceutical composition for obtaining a coronary artery vasodilating effect in a human or animal in need thereof, which comprises an effective amount of the compound according to claim 6 and a pharmaceutically acceptable diluent or carrier therefor.

* * * * *